United States Patent [19]

Thomas

[11] Patent Number: 5,222,491

[45] Date of Patent: Jun. 29, 1993

[54] TEMPORARY PATIENT VENTILATOR

[76] Inventor: Samuel D. Thomas, P.O. Box 3964, Pensacola, Fla. 32516

[21] Appl. No.: 889,985

[22] Filed: May 29, 1992

[51] Int. Cl.⁵ ............................................. A61M 16/08
[52] U.S. Cl. .......................... 128/205.13; 128/204.18; 128/205.16; 417/394; 417/478
[58] Field of Search ....................... 128/200.24, 204.18, 128/205.13, 204.28, 205.14, 205.16, 205.17, 206.28, 207.14, 207.17, DIG. 12; 417/394, 478; 604/131, 153

[56] References Cited

U.S. PATENT DOCUMENTS

| 283,137 | 8/1883 | Nevius | 128/205.16 X |
|---|---|---|---|
| 2,907,322 | 10/1959 | Hay | 128/204.28 |
| 3,062,153 | 11/1962 | Losey | 417/478 X |
| 3,530,857 | 9/1970 | Miczka | 128/205.13 |
| 3,841,327 | 10/1974 | Hay | 128/204.28 |
| 3,932,066 | 1/1976 | Eyrick | 417/328 |
| 4,374,521 | 2/1983 | Nelson | 128/205.13 |
| 4,867,151 | 9/1989 | Bird | 128/201.17 |
| 4,886,056 | 12/1989 | Simpson | 128/201.25 |
| 4,899,740 | 2/1990 | Napolitano | 128/202.22 |
| 4,903,694 | 2/1990 | Hager | 128/204.15 |
| 4,905,687 | 3/1990 | Ponkala | 128/204.21 |

FOREIGN PATENT DOCUMENTS

| 10893 | 5/1980 | European Pat. Off. | 128/205.13 |
|---|---|---|---|
| 7908020 | 6/1981 | Netherlands | 128/205.14 |
| 2174608 | 11/1986 | United Kingdom | 128/205.17 |

Primary Examiner—Edgar S. Burr
Assistant Examiner—Eric P. Raciti
Attorney, Agent, or Firm—Richard C. Litman

[57] ABSTRACT

A temporary patient ventilator is a modified version of the widely used air-mask-bag-unit (AMBU). The modified AMBU has guy wires attached to the inside resilient walls of the airbag which are pulled to collapse the airbag. A drive is used to alternately pull on the guy wires and then release them automatically. This new automated airbag unit system allows hands free operation of the ventilation device for short periods of time. The drive has rechargeable batteries so that the temporary ventilator is completely mobile.

20 Claims, 5 Drawing Sheets

TEMPORARY PATIENT VENTILATOR

BACKGROUND OF THE INVENTION

1. Field of the Invention

This invention pertains to battery operated, mobile patient ventilators for use on patients while the patients are temporarily disconnected from a stationary artificial respirator. More particularly, it pertains to patient ventilators using a modified version of the manually operated conventional air-mask-bag-units, herein referred to as AMBUs, so as to allow both an automatic operation as well as a manual operation of the modified AMBU.

2. Description of the Relevant Prior Art

Mobile powered respirators and ventilators are used to provide clean and healthy air to the user with little to no breathing effort on the part of the user. Such devices often depend on a mobile expendable power source, such as rechargeable batteries, in order to power a motor connected to a fan so as to create a high pressure region of air to be taken in by the user.

U.S. Pat. No. 4,867,151 issued Sep. 19, 1989 to Forrest M. Bird discloses a mobile self-contained ventilator which inhibits water from condensing in the one or more cartridges containing the pressurized air.

U.S. Pat. No. 4,886,056 issued Dec. 12, 1989 to Keith Simpson discloses a positive pressure filter respirator in which an electric motor drives a fan which draws air through the filter canister into the mask.

U.S. Pat. No. 4,899,740 issued Feb. 13, 1990 to Michael L. Napolitano discloses a portable respirator system carried around a waist belt.

U.S. Pat. No. 4,903,694 issued Feb. 27, 1990 to Volker Hager discloses a portable ventilating apparatus for a protective suit in which a blower supplies air to ventilate a suit as well as supplies air to a mask.

U.S. Pat. No. 4,905,687 issued Mar. 6, 1990 to Jorma Ponkala discloses a respirator in which a sensor monitors a parameter of the motor operating a blower to provide feedback to a circuit driving the motor, thereby providing a constant output of the blower under increase load conditions due to the clogging of the filter.

None of the prior art of record discloses the features by which an air-mask-bag-unit is modified to provide both manual as well as automatic operation of the patient ventilator of the present invention.

SUMMARY OF THE INVENTION

Thus, it is an object of the present invention to provide a temporary patient ventilator which allows for the manual or automatic operation of an AMBU.

It is another object of the present invention to provide hands off operation of the AMBU in its automatic mode of operation, thereby freeing medical personnel to perform other tasks.

Another object of the present invention is to provide variable stroke rates of the AMBU during automatic operation thereof.

Yet another object of the present invention is to provide variable stroke volumes of the AMBU to regulate the volume of air delivered per stroke.

It is still another object of the present invention to provide an audible sound indicator each time the patient exhales.

These and other objects of the present invention will become clear by reviewing the following drawings and specification.

The present invention is a unique temporary ventilating device which allows medical personnel to ventilate a patient during those times when the patient respiratory assistance is not being supported by a standard ventilator. Such situations arise when a ventilator dependent patient undergoes x-ray procedures or magnetic residual imaging (MRI) scans or computer aided tomography scans. Such situations could also include ventilator circuit change outs, transfers, or medical emergencies. With the temporary ventilator of the present invention, all of these situations require only one medical attendant.

The conventional AMBU requires one person just to operate the unit. In the present invention an AMBU is modified so that the bag is squeezed by tensioning three cables attached to the inside walls of the bag through a tube down the center of the bag so as to collapse the bag when the cables are pulled. By releasing the tension on the cables, the bag inflates in the same manner the conventional AMBU bag would if it were manually squeezed and released. By connecting the cables to an automatic drive mechanism with a portable power source, a hands-free operation of the modified AMBU is achieved, thereby providing an automated airbag unit.

In a hospital intensive care setting, a ventilator circuit must be changed every forty-eight (48) hours. The circuit is the plastic disposable tubing that runs from the ventilator to the patient. Each time the circuit is replaced one respiratory therapist must manually ventilate the patient using an AMBU and one therapist must change the circuit and test the ventilator. The total time spent for changing a circuit is approximately ten (10) minutes. With the automated airbag unit of the present invention, one therapist can change out a circuit while the automated airbag unit ventilates the patient automatically, thus saving valuable time and manpower.

The temporary ventilator of the present invention also finds use in a home environment of a ventilator dependent patient. The temporary ventilator of the present invention would allow freedom of movement of such a patient without the need of a cumbersome portable ventilator or the immediate presence of medical personnel.

DETAILED DESCRIPTION OF THE PREFERRED EMBODIMENTS

Figures 1, 2:
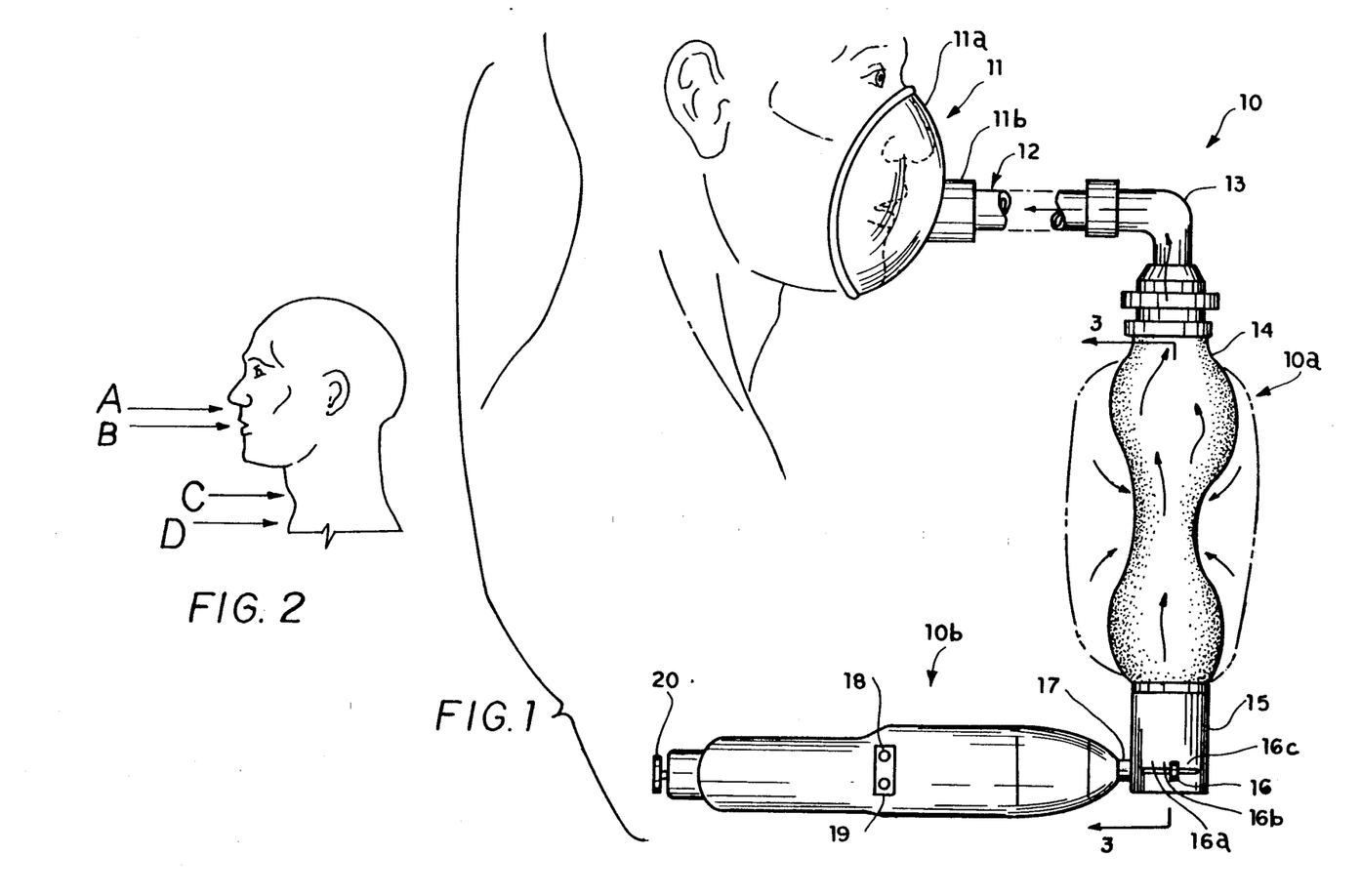
FIG. 1 is an environmental view of a first embodiment of the automated airbag of the present invention connected to a patient by an air mask.
FIG. 2 is a drawing showing alternate locations for connecting the present invention to the patient.

As shown in FIG. 1, an automated airbag unit system 10 has integral drive unit 10b connected to the airbag unit 10a of the first embodiment of the present invention. A hexagonal cover 17 of the drive unit 10b fits over a smaller hexagonal cover (not shown in FIG. 1) of the airbag unit 10a. The hexagonal cover of the drive unit 10b is locked into position by a form fit over the smaller hexagonal cover of the airbag unit 10a. By this connection the integral drive unit 10b in cooperation with a timing box 15 causes the resilient airbag 14 to be collapsed a predetermined distance about its middle during a first predetermined period of time and to expand back to its original shape during a second period of time. The means for accomplishing this task for the first embodiment will be explained in conjunction with FIGS. 3, 4, and 8.

The integral drive unit 10b provides a constant cyclical motion to the timing box 15, which translates that motion to mechanical attachments (not shown in FIG. 1) connected on the inside of the resilient airbag 14. The airbag 14 is cyclically collapsed and expanded at predetermined intervals, the first part of the predetermined interval occurring during each first predetermined period of time and the second part of each predetermined interval occurring during the second predetermined period of time.

The integral drive unit 10b is provided with a variable speed control input adjustable by a manually operated knob 20 to cause the drive unit to increase or decrease the predetermined intervals as discussed in conjunction with FIG. 8 below. This in turn varies the rate at which the resilient airbag 14 is collapsed and expanded. A manually operated slide 16 on the timing box 15 can be adjusted to control how completely the airbag 14 is collapsed. There are three notches 16a, 16b, and 16c for locking the manually operated slide 16 into three set positions when mated with a locking bump (not shown) of the manually operated slide 16. The integral drive unit 10b is also provided with an on/off switch 18 and a recharger connection 19.

Each time the resilient airbag 14 is collapsed air is pushed into an air outlet 13 connected to an airtube 12. A respiratory connection to the patient is illustrated in FIG. 1 by an airmask 11 having a first end covering the nose and mouth of a patient and a second end connected to the airtube for receiving the pushed air, thereby providing the pushed air to the lungs of the patient. The volume of air provided to the patient increases with an increase of the predetermined distance the airbag is collapsed about its middle. Thus, the manually operated slide 16 controls the amount of volume of air provided to the patient during each cycle and the manually operated knob 20 controls the rate at which air is provided to the patient.

As shown in FIG. 2, other respiratory connections to a patient rather than an airmask may be used in the present invention. For example, a nasothracheal tube may be passed through the patients nose at the location A, or a orotracheal tube may be inserted at location B of the patients mouth. Other connections to the neck are also possible such as an esophageal obturator airway connection at location C or a tracheostomy tube connection at location D. All of the above respiratory connections are known in the respiratory art.

Figure 3:
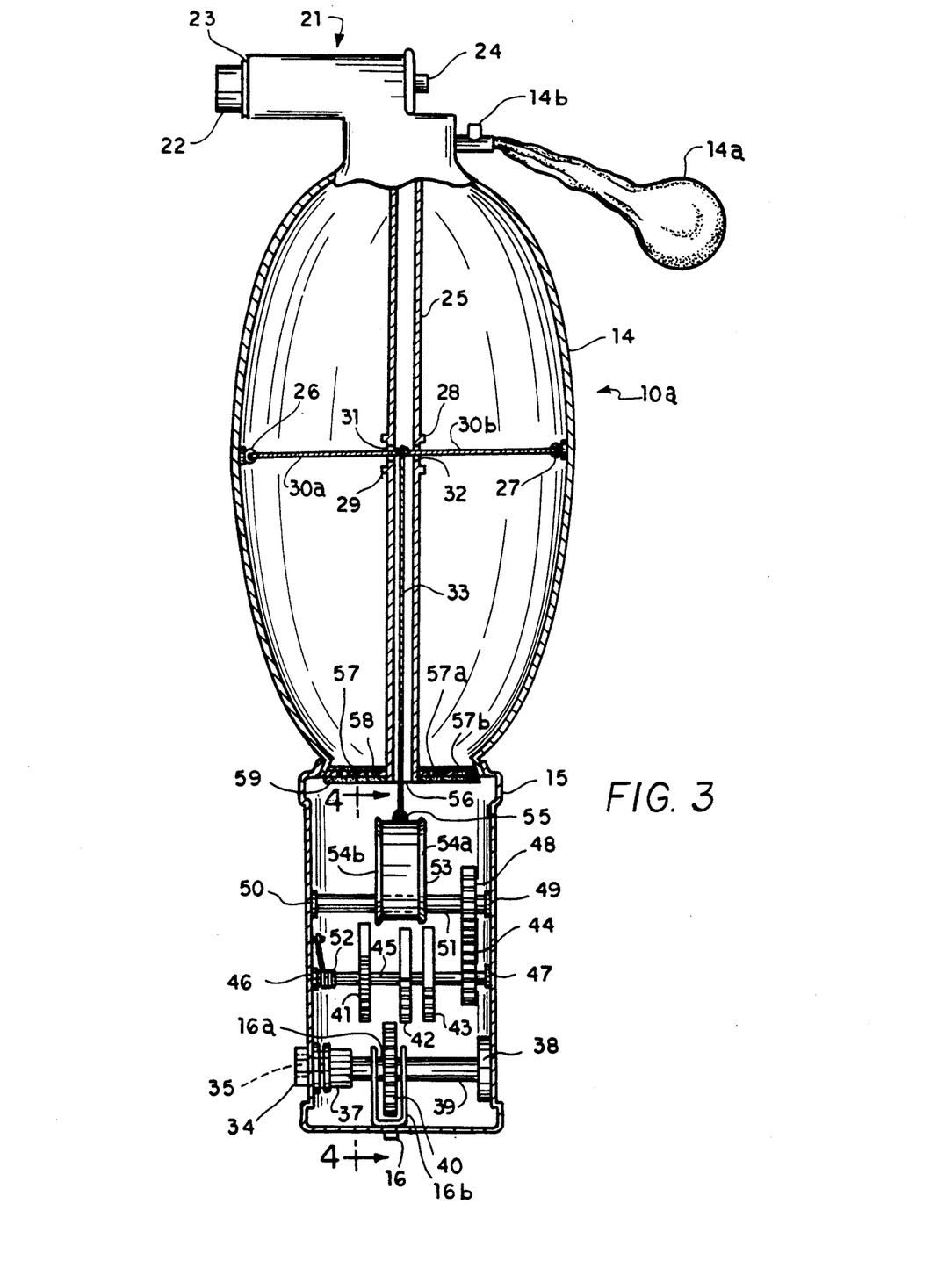
FIG. 3 is a cross-sectional view of the airbag and timing box along line 3—3 of FIG. 2 with an alternate air outlet usable with the present invention.

FIG. 3 shows a cross-sectional view of the timing box 15 with a different air outlet 21 connected on top to illustrate optional features which may be incorporated with the airbag unit 10a such as a positive end expiratory pressure (PEEP) valve which may be manually adjusted to provide a variable back pressure as the patient exhales. A one-way valve (not shown) is part of the air outlet 21 and prevents the exhaled air from entering the airbag unit 10a, while at the same time allowing air to exit the airbag unit 10a when squeezed. The exhaled air goes out the PEEP valve as it is directed from the patient connection to the airtube and then the air outlet 21. The airtube (not shown) connects to the air outlet 21 by inserting one end of the airtube over around surface 22.

The air outlet 21 as described in a conventional air outlet provided on AMBUs sold by Resperonics, Inc. An expiratory audible indicator 23 of the present invention may be connected to the air outlet 21 as shown. The audible indicator 23 is a one way valve connected at the end of the round surface 22 in contact with the end of the airtube placed over the round surface 22. The expiratory audible indicator 23 allows a portion of air to pass over it when the air is directed from the airtube to the air outlet 21. In this way, as the patient exhales an audible indicator is given that the patient is still breathing. This would work even when a patient is breathing spontaneously. The one-way valve connected to the air outlet 21 from the resilient airbag 14 opens when the patient inhales since the pressure on the air outlet 21 side would be less than the pressure within the resilient airbag 14. The air outlet 21 also has an oxygen reservoir bag 14a and an oxygen inlet 14b connectible to an external oxygen supply source. Both the reservoir bag 14a and the oxygen inlet 14b lead directly into the cavity of the airbag 14.

As shown in FIG. 3, the resilient airbag 14 has a guy wire 30a connected at one end to an attachment 26, which in turn is connected to the inner wall of the resilient airbag 14. Another guy wire 30b is connected to the attachment 27 also connected to the inner wall of the resilient airbag 14, but in a location of the inner wall opposite that location of attachment 26. The guy wire 30a enters a hollow tube 25, which extends along the center axis of the resilient airbag 14, through hole 31. The guy wire 30b enters hollow tube 25 through hole 32. A guy wire portion 33 which is connected to the guy wires 30a and 30b runs down the length of the hollow tube 25 to a substantially airtight opening 56 consisting of a hole just large enough to fit the guy wire portion 33 loosely therethrough. Alternatively, the guy wire portion 33 could be a part of one or more of the guy wires 30a and 30b.

During the first predetermined period of time during each cycle of operation of the airbag unit system 10, a downward tension is placed on the guy wire portion 33 so that the guy wire portion 33 is pulled down the hollow tube 25 towards the timing box 15. The guy wires 30a and 30b are consequently pulled into the hollow tube through the holes 31 and 32 in a radial direction of the center axis of the resilient airbag 14. Protective sleeves 28 and 29 are placed around the hollow tube 25 to add structural strength to the tube in the vicinity of the holes 31 and 32. Each guy wire 30a and 30b then pulls on the attachments 26 and 27, causing the resilient airbag 14 to collapse about its middle in a radial direction to the center axis of the resilient airbag 14. This pushes air into the air outlet 21.

During the second predetermined period of time of each cycle, tension on the guy wire portion 33 is relaxed and the resilient airbag 14 assumes its normally expanded shape. During this process, air enters the resilient airbag 14 through a one way valve 58 located on top of a circular portion 57. The one way valve 58 is a flexible plastic flap. The portion 57 has a set of holes 57a along an inner radius and another set of holes 57b along an outer radius. The one way valve 58 allows air to enter into the resilient airbag 14 therethrough, while preventing air from exiting therethrough in the conventional manner. The air which comes through the slot by which the manually operated slide 16 is adjusted is filtered by a filter 59 on the wall portion 57 so that foreign matter does not enter the resilient airbag 14.

The operation of the timing box 15 will now be described in conjunction with FIG. 3. The hexagonal cover 17 of the drive unit 10b fits over the hexagonal cover 34 of the timing box 15. Within the hexagonal cover 34 is a hexagonal drive connection. Within the hexagonal cover 17 is a hexagonal shaped connector which mates with the hexagonal drive connection. The integral drive unit 10b rotates the drive connector at a constant angular rate as set by the manually operated knob 20. The drive connector, when engaged with the drive connection of the timing box 15, receives the angular rotation of the drive connection and rotates the shaft of the drive connection which goes through a bearing 36 attached to the right wall of the timing box 15. The shaft of the drive connection is connected to a hexagonal shaped shaft 39 by a receptor 37 at the end of the shaft of the drive connection. The other end of the shaft is connected to a bearing 38 fastened to the left wall of timing box 15. The hexagonal shaped shaft 39 rotates a main gear 40 which is connected to a bearing 16a slidably fitted around the hexagonal shaped shaft 39. The bearing 16a has both of its ends attached to forked arms 16b. Both bearing 16a and forked air 16b are part of the manually operated slide 16. The manually operated slide is adjustable to a location placing the main gear 40 in contact with one of the gears 41, 42, or 43. Each of the notches 16a, 16b, 16c as shown in FIG. 1 places and locks the main gear 40 in contact with one of the gears 41, 42, or 43 when mated with a locking bump which falls into the notches as the manually operated slide 16 is moved from its extreme positions. The gears 41, 42, and 43 are used to control the volume of air delivered to the patient during the first predetermined period of time of each cycle the timing box 15 is in operation. This is accomplished in the following manner.

Figure 4:
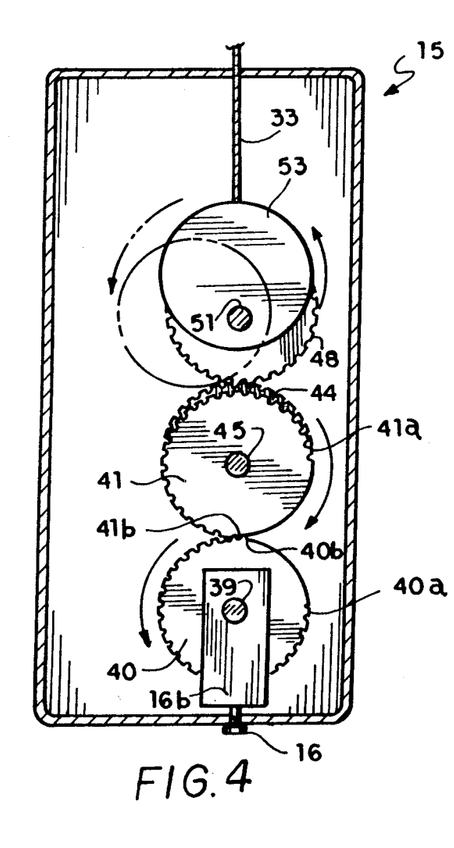
FIG. 4 is a cross-sectional view of the timing box along lines 4—4 of FIG. 3.

As shown in FIG. 3 and FIG. 4, the main gear 40 as well as the gears 41, 42, and 43 each have a toothed region and a smooth region. For example, as shown in FIG. 4, the main gear 40 has a toothed region beginning with a first tooth 40a and ending with a last tooth 40b when the main gear 40 is rotated in the direction indicated. If gear 41 was engaged with the main gear 40, then gear 41 would have a toothed region beginning with tooth 41a and ending with tooth 41b. In the preferred first embodiment, the main gear 40, as well as gears 41, 42, and 43, all have the same size gears. While main gear 40 and gear 41 are illustrated as having three quarters of their outer surface as being a toothed region, while only one quarter is smooth, any ratio of toothed region to smooth region may be used as long as the main gear has at least as many teeth as any one of the gears 41, 42, and 43 for reasons to be discussed below.

Each of the gears 41, 42, and 43 are rigidly connected to a shaft 45, which in turn has one end connected to a bearing 46 fastened to the right side wall of timing box 15 and the other end connected to a bearing 47 fastened to the left side wall of the timing box 15. Another shaft 51 having a cam 53 rigidly connected to it has one end connected to a bearing 50 fastened to the right side wall of timing box 15 and the other end connected to a bearing 49 fastened to the right side wall of the timing box 15. The shaft 51 has a transfer gear 48 rigidly connected to it which engages another transfer gear 44 rigidly connected to shaft 45. In this manner, angular motion of shaft 45 is transferred to shaft 51 during the first predetermined period of time.

For example, as shown in FIG. 4, at the end of the first predetermined period of time, the last tooth 40b of the main gear 40 engages the last tooth 41b of the gear 41. Initially the first teeth 40a and 41a of the main gear 40 and gear 41 respectively were engaged. As the main gear 40 rotates in the direction shown, gear 41 is rotated in the opposite direction. Eventually, the last tooth 41b and 40b are engaged at the end of the first predetermined period of time. During the first predetermined period of time, as the shaft 39 is rotated by the integral drive unit 10b as described above with the main gear 40 is engaged with the gear 41, the cam 53 is rotated in the direction shown from its rest position as shown in FIG. 3. The cam 53 is kept in its rest position by a spring 52 which is attached to the shaft 45 and also to the right side wall of timing box 15. The spring 52 produces no angular force on the shaft 51 when the shaft is at a predetermined angular position with the cam 53 in its rest position. Since the cam is attached to the guy wire portion 3 through an attachment 55 connected to the cam 53, as the cam 53 rotates it pulls on the guy wire portion 33 along a cam surface of the cam 53. Flanges 54a and 54b are used to prevent the guy wire portion 33 from slipping off the cam surface. Also, as the cam 53 rotates, the spring 52 applies an angular force in the opposite direction of rotation.

With the last tooth 40b of the main gear 40 engaging the last tooth 41b of the gear 41, the cam is rotated as shown in FIG. 4, pulling the guy wire portion 33 the predetermined distance discussed above. As the main gear 40 rotates further in the direction shown in FIG. 4, the smooth surface of the main gear starting just after the last tooth 40b and ending just before the first tooth 40a is engaged with the gear 41. Since the spring 52 has applied an angular force in the opposite direction to the direction shaft 51 was rotated, gear 41 rotates in the opposite direction as shown in FIG. 4 during a second predetermined period of time in which the smooth surface region of the main gear 40 engages the gear 41. The spring 52 is designed to position cam 53 in its rest position before the end of the second predetermined period of time and the resilient airbag is designed to be fully expanded before the end of the second predetermined period of time as the guy wire portion 33 is pulled back up through the substantially airtight hole 56. With the cam back in its rest position, the first tooth 41a of the gear 41 is engaged with the smooth region of the main gear 40 until the beginning of the next cycle in which the first tooth 40a of the main gear 40 engages the first tooth 41a of the gear 41 once again during another first predetermined period of time.

If the gear 41 had fewer teeth than the main gear 40, then the last tooth of gear 41 would engage one of the teeth before the last tooth of main gear 40 and then every tooth after that one tooth of main gear 40 up to and including the last tooth would push the back of the last tooth of gear 41 until it rose above the top of the last tooth and then the gear 41 would rotate in the opposite direction just enough to engage the back of the last tooth of gear 41 with another tooth of main gear 40. In this way the gear 41 is substantially held in position until the smooth region of main gear 40 allows gear 41 to rotate in the opposite direction the toothed region of main gear 40 was rotating it as described above. The more teeth the gear engaged with the main gear has, the more the guy wire portion 33 is pulled resulting in more air being supplied to the patient each cycle.

Figures 5, 7:
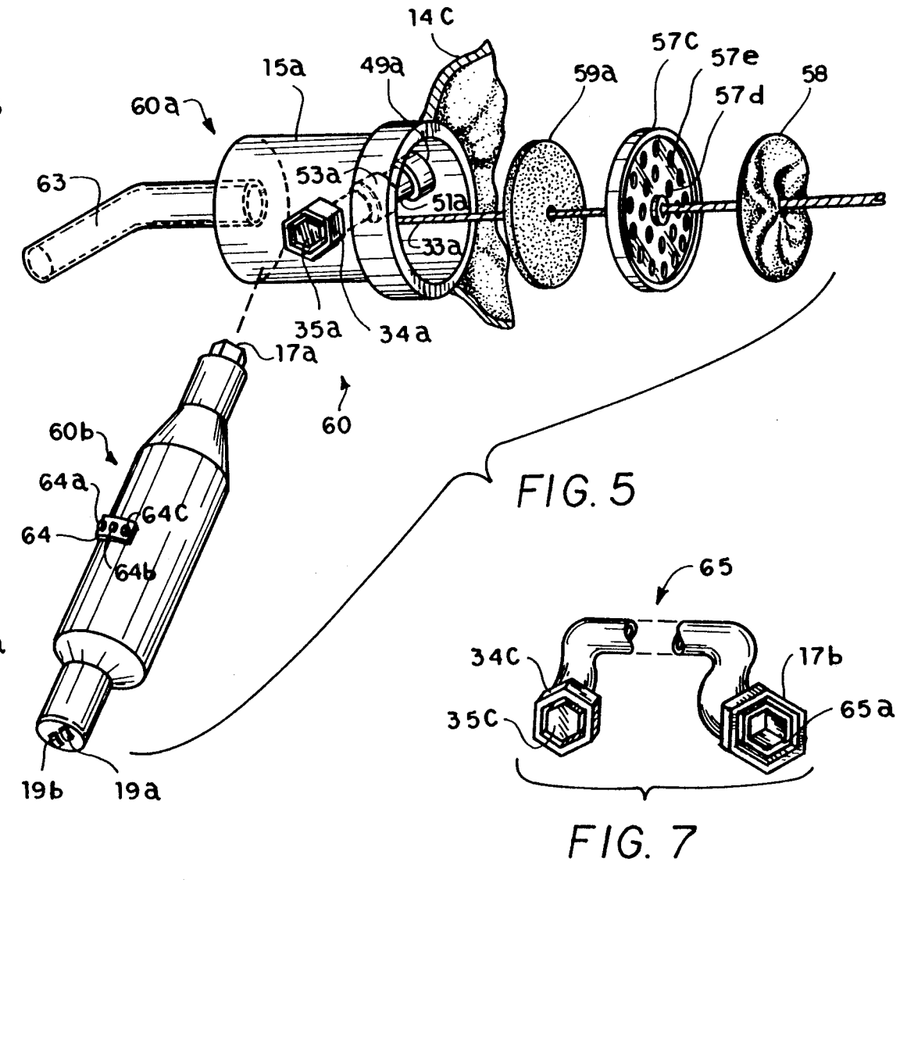
FIG. 5 is a partial view of a second embodiment of the automated airbag of the present invention.
FIG. 7 shows the end views of the flexible drive cable.

A second embodiment of the present invention is shown in FIG. 5. The second embodiment is somewhat similar to the first embodiment. In the second embodiment, a single shaft 51a is used in conjunction with an integral drive unit 60b which reverses the direction of the drive connection during the second predetermined period of time instead of rotating the drive connection at a constant angular rate as done in the first embodiment. This greatly simplifies the timing box 15a. The shaft 51a is simply attached at one end by a bearing 49a connected to a side of the wall of timing box 15a, and at another end by another bearing attached to the other side of the wall of timing box 15a. Cover 17a is the same as cover 17 of the first embodiment. Cover 17a fits over cover 34a to form a snug fit thereover. The drive unit 60b imparts circular motion to a drive connection within the cover 17a (not shown) which engages the drive connector 35a to turn the shaft 51a in the same manner as the first embodiment.

The circular portion 57a is the same as the portion 57 as used in the first embodiment, where a one way valve 58a is allowed to open into the cavity of the resilient airbag 14a as air enters through holes 57e and 57d, but can not open in the opposite direction into the cavity of timing box 15a. A filter 59a is used behind the door in the same manner as filter 59 was used in the first embodiment. Also shown in FIG. 5 is an attachable air reservoir connection 63 for supplying oxygen enriched air to the patient.

As shown in FIG. 5, the integral drive unit 60b is supplied with manually operated controls 64, including switch 64a for turning the integral drive unit 60b on and off, as well as a knob 64b for controlling the rate of each cycle, and a knob 64c for controlling the volume of air supplied during each cycle by moving the guy wire 33a in the same manner as the guy wire 33 was moved in conjunction with the first embodiment. Integral drive unit 60b is also supplied with recharger connections 19a and 19b.

Figure 6:
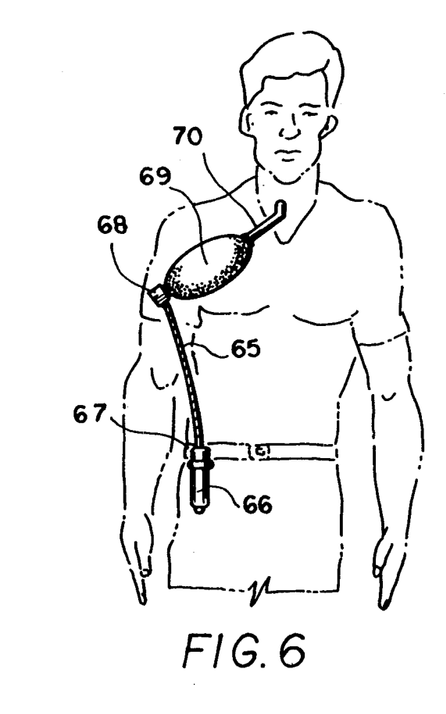
FIG. 6 is an environmental view of the present invention using a flexible drive cable as an alternate connection of the drive unit to the timing box usable with all embodiments of the present invention.

FIGS. 6 and 7 show a third embodiment of the present invention in which an airbag 69 and timing box 68 are much the same as either airbag 14 and timing box 15 of the first embodiment or airbag 14a and timing box 15a of the second embodiment. The main difference between the third embodiment and the first two embodiments is that a flexible drive shaft connection 65 is used between the drive connection of the integral drive unit 66 and the drive connector of the timing box 68. As shown in FIG. 7, the flexible drive shaft connection 65 has an outer portion being a flexible tubing in which is located a flexible wire with one end connected to a rotary head 35c located within a cover 34c. The rotary head 35c is identical to the drive connector 35a of the second embodiment as well as drive connector 35 of the first embodiment. At the other end of the flexible wire within the flexible tubing 65 is a rotary head 65a identical to the drive connection of the first two embodiments. Cover 17b is identical to cover 17 of the first embodiment and cover 17a of the second embodiment. In this way the cover 17b will fit over the cover of the drive connector of the timing box 68 so as to engage the rotary head 65a. At the other end of the flexible drive shaft 65, the rotary head 35c engages the drive connection by slipping the cover 34c into the cover of the integral drive unit 66. Any rotation of the rotary head 35 causes an equal amount of rotation of the rotary head 65. Thus, the flexible drive shaft 65 allows the integral drive unit to drive the timing box 68 even when not directly attached thereto.

As shown in FIG. 6, by attaching the integral drive unit 66 to the belt 67, the weight of the unit is supported by the belt 67 worn by the patient. A tracheostomy tube connection 70 is used to supply air to the patient by the airbag 69 in a manner discussed above. The timing box 68, airbag 69, and tracheostomy tube connection 70 may be attached to the shirt of the patient in any known manner. This allows the patient to move above while hands-free respiration is provided by the device of the third embodiment.

Figure 8:
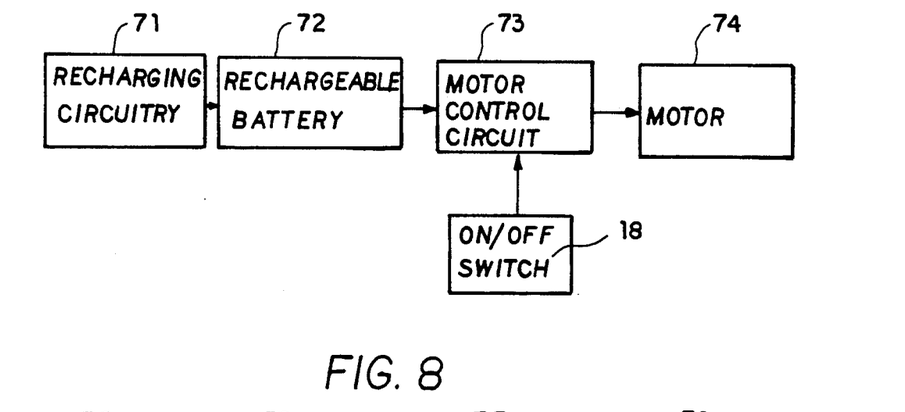
FIG. 8 shows a block diagram of the drive unit for the first embodiment of the present invention.

FIG. 8 is a block diagram of the internal electronics of the integral drive unit 10b of the first embodiment. Recharging circuitry 71 has a regulated d.c. voltage input from recharger connection 19 shown in FIG. 1 for recharging rechargeable battery 72. Rechargeable battery 72 supplies motor control circuit 73 with a voltage to drive motor 74. Motor control circuit 73 is has an input from the knob 20 which controls the amount of drive supplied to the motor 74. For example, the knob 20 could be connected to a variable resistor which taps off a certain amount of voltage to be supplied to the motor 74. Motor 74 has a rotating shaft connected to the drive connection of the integral drive unit 10b. By varying the input from knob 20, the shaft of the motor 74 is driven at different rotations per minute. On/Off switch 18 causes the motor control circuit 73 to disconnect the battery from the motor 74.

Figure 9:
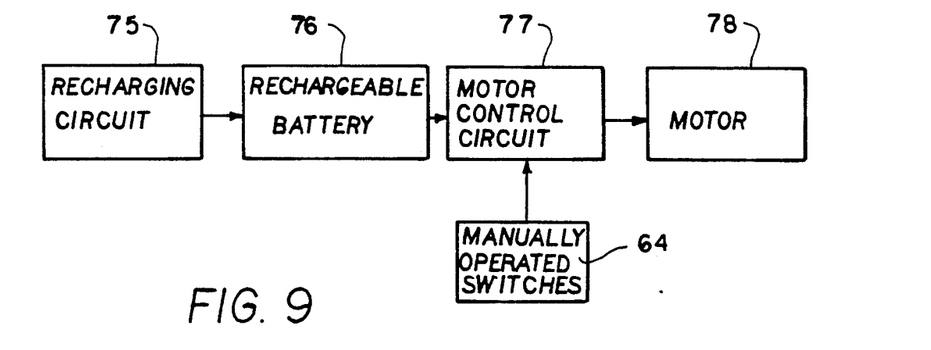
FIG. 9 shows a block diagram of the drive unit for the second embodiment of the present invention.

FIG. 9 is a block diagram of the internal electronics of the integral drive unit 60b of the second embodiment. Recharging circuit 75 receives a regulated d.c. voltage from recharger connections 19a and 19b shown in FIG. 5 to recharge the rechargeable battery 76. The motor control circuit 77 has inputs from the manually operated controls 64 shown in FIG. 5. Motor 78 is a reversible motor supplied with power by the rechargeable battery 76 under the control of motor control circuit 77. Control circuit 77 causes the motor 78 to rotate in one direction for a predetermined amount of revolutions and then go the same number of revolutions in the opposite direction. Manually operated knob 64c varies the amount of revolutions the motor 77 rotates before switching directions. Manually operated knob 64b controls the rate at which the motor 77 switches directions. Manually operated switch 64a is an on/off switch which alternately allows or prevents power from going to the motor 77 from the rechargeable batteries 76. Motor control circuit 77 could be any mechanical or electrical controller for accomplishing the above tasks.

Figure 10:
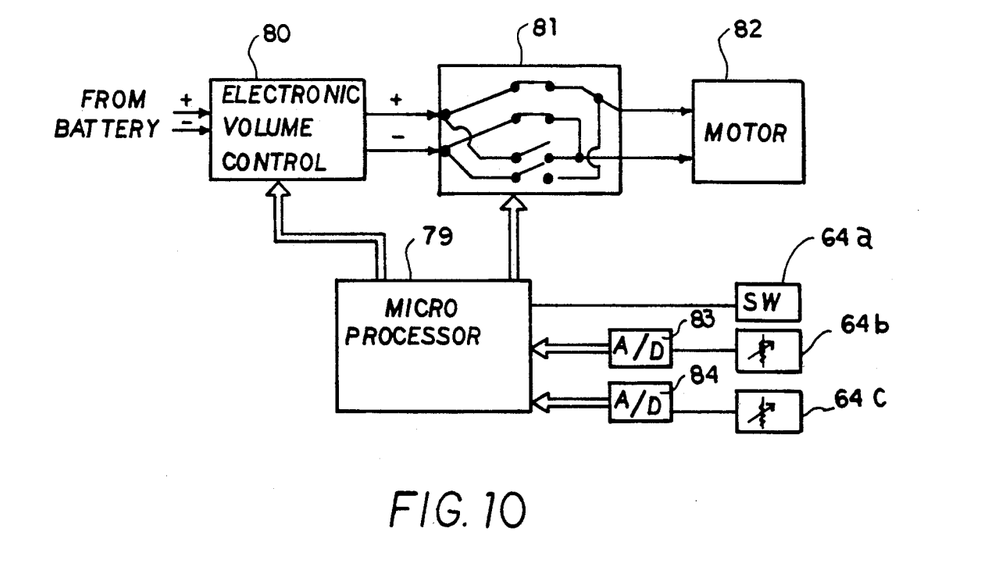
FIG. 10 shows the details of the motor control circuit of the second embodiment of the present invention.

As shown in FIG. 10, in the preferred second embodiment motor control circuit 77 uses a microprocessor 79 to control the amount of current as well as the polarity of the current going to motor 78. Switch 64a is an on/off switch which causes the microprocessor 79 to set electronic volume control circuit 80 to pass no current from the battery to relay switch 81 when the switch 64 is manually turned off. Otherwise, manually operated knob 64b controls a variable resistor with an output going to an analog to digital (A/D) converter 83. The A/D converter 83 supplies microprocessor 79 with a digital signal giving an indication as to what level to set the electronic volume control 80 and also how often to switch the polarity of the motor 82 through the use of relay switch 81. Electronic volume control 80 is a variable resistor which is digitally controlled as is known in the art. Since the electronic volume control 80 is in series with the motor 82, then the lower the resistance of the electronic volume control is set at, the more current is supplied to the motor 82. The relay switch 81 is used to switch the polarity of the motor 82, thereby reversing the direction that the shaft of the motor rotates. Manually operated knob 64c has an output connected to an A/D converter 84 for supplying microprocessor 79 with a digital signal. Since manually operated knob 64b controls the rate of each cycle, herein referred to as X in cycles per minute (cpm), while manually operated knob 64 controls the number revolutions the shaft is rotated in each cycle in one direction and then the other direction, herein referred to as Y in revolutions, then the speed of the motor, herein referred to as Z revolutions per minute (rpm), as controlled by the electronic volume control 80 is increased whenever X or Y increases. In fact, Z is proportional to X times Y. The rate at which the relay switch 81 is switched is only a function of X. For example, if X is 20 cpm while Y is 0.25 revolutions, 45 degrees in one direction and 45 degrees in the opposite direction, then if the manually controlled knob 64b were set to double the rate while the manually controlled knob 64c was not moved, the electronic volume control 80 would double the speed of the motor 82 so that Z is 40 cpm while the switching rate of the relay switch 81 would also double so that Y is still 0.25 revolutions. However, if the manually controlled know 64b were not moved while the manually controlled knob 64c were moved to double the Y, then Z would double but the switching time for the relay switch 81 would stay the same. In this way the cam 53a would be move 90 degrees in one direction before being moved 90 degrees the other direction. This would occur 20 times a minute in the above second example. An algorithm as demonstrated in the above examples is used in microprocessor 79 to control the electronic volume control 80 and the relay switch 81 as discussed in the above examples.

Figure 11:
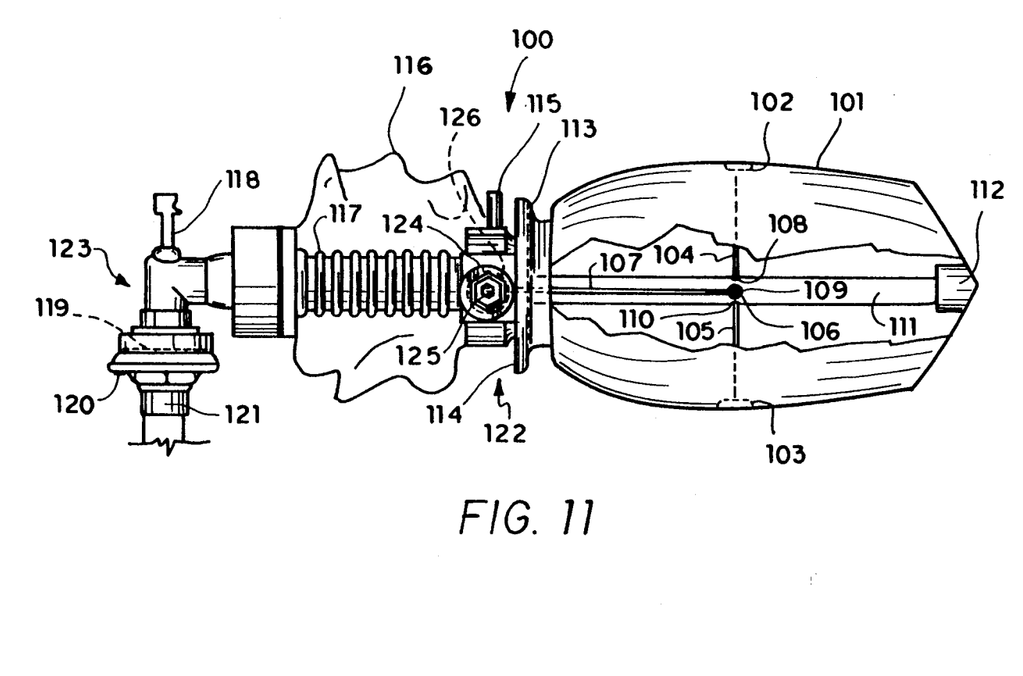
FIG. 11 shows a third embodiment of the automated airbag of the present invention.

FIG. 11 shows a fourth embodiment of the automated airbag of the present invention usable with the integral drive unit 60b. The fourth embodiment is a modified AMBU sold by Respironics, Inc., model number 412040. Like the other embodiments, the automated airbag unit 100 has a resilient airbag 101. The resilient airbag 101 has an opening at one end in which a first tube 122 is inserted. When the resilient airbag 101 is squeezed, air is pushed up the first tube 122, to a second flexible tube 117 which is attached to the second end of the first tube 122. The air then flows to a respiratory connector 123 which has a first end 121 connectable to a patient as described in conjunction with FIG. 2 and a second end connected to the second flexible tube 117. A conventional one way valve 119, which is part of the Respironics model, allows air to flow to the patient, while preventing the patient from exhaling into the resilient airbag 101. Instead, the exhaled air is directed to a noise maker 120 attached to the respiratory connector 123 in front of the one way valve 119. The noise maker gives an audible indication each time the patient exhales. The respiratory connector 123 also has a PEEP valve adjustment 118 to provide a back pressure as the patient exhales as described above.

As the resilient airbag 101 returns to its normally expanded position, air enters the airbag 101 through an opening 114 of the first tube. A one way valve 113, which is part of the Respironics model, allows air to enter into the airbag therethrough, while preventing air to exit therethrough. In this manner all air exiting the airbag 101 goes to the respiratory connector 123, while all air enter the airbag 101 comes through the one way valve 113. An oxygen inlet 115 connectable to an external oxygen supply source also has a airflow path to the one way valve 113. In this manner oxygen enriched air may be provided to the patient. A reservoir volume bag 116 is provided to store any excess oxygen which enters through the oxygen inlet 115. The bag has one end connected to the respiratory connector 123 and another end connected to the first tube.

The modified airbag unit 100, has four guy wires connected to the inside of the airbag 101. As shown in FIG. 11, each guy wire is attached to the inside of the airbag 101 by any conventional attachment. While only three of the four guy wires are illustrated in FIG. 11, each guy wire has one end attached to the inside of the resilient airbag 101. For example, guy wires 104 and 105 are attached at opposite ends by attachments 102 and 103, respectively. Guy wire 106 is also attached to the airbag, while another guy wire (not shown), is attached at an opposite end of guy wire 106. Each guy wire enters a hollow tube 111 through holes in the middle of the tube, such as holes 108, 109, and 110. At one end, the hollow tube 111 is attached to the resilient airbag 101 by any conventional attachment 112, and at an opposite end, to the first tube 122 by any conventional means.

Each of the four guy wires are attached to one end of another guy wire 107 located inside the hollow tube 111. The opposite end of the guy wire 107 is attached to a cam 126 which is connected to a drive connector 125 in the same manner as the second embodiment of FIG. 5. Around the drive connector has a cover 124 identical to cover 34a of the second embodiment.

The embodiments as presented above are not to be construed as limiting the scope of the invention which encompasses all of the embodiments as present in the appended claims.

I claim:

1. A ventilating device comprising:
   a resilient airbag having means for biasing said airbag to a normally expanded state and said airbag being collapsible about a center axis, said resilient airbag further having a first airbag end and a second airbag end located along said center axis;
   a first airbag opening at said first airbag end;
   an air outlet connected to said first airbag opening;
   a respiratory connector having a first respiratory end connectable to a patient and a second respiratory end having an air passageway in fluid communication with said first respiratory end;
   an airtube having a first airtube end connected to said air outlet and a second airtube end connected to said second respiratory end;

a first one-way valve means located within said respiratory connector for allowing air to exit said resilient airbag through said first respiratory end while preventing air from entering said resilient airbag through said first respiratory end;

a second airbag opening into said resilient airbag;

an air inlet connected to said second airbag opening;

a second one-way valve means connected between said second opening and said air inlet for allowing air to enter said resilient airbag through said second airbag opening while preventing air from exiting said resilient airbag through said second airbag opening;

a plurality of mechanical attachments connected to said resilient airbag, said attachments including means for collapsing said airbag when moved in a first direction; and actuator means for cyclically engaging said means for collapsing such that said plurality of mechanical attachments move a predetermined distance in said first direction for a first predetermined period of time to overcome said means for biasing said airbag and subsequently disengaging said means for collapsing, thereby allowing said means for biasing said airbag to expand said airbag for a second period of time, wherein air enters said resilient airbag through said air inlet and said mechanical attachments move said predetermined distance in a second direction opposite said first direction.

2. A ventilating device as claimed in claim 1, further comprising:

means for manually adjusting said predetermined distance so as to allow the user control over the volume of air supplied to a patient connected to said first respiratory end during each cycle; and means for manually adjusting said first predetermined period of time and said second predetermined period of time so as to allow the user control over the length of time between each cycle.

3. A ventilating device as claimed in claim 2, wherein said respiratory connector comprises an air mask.

4. A ventilating device as claimed in claim 2, wherein said respiratory connector comprises an orotracheal tube.

5. A ventilating device as claimed in claim 2, wherein said respiratory connector comprises a nasotracheal tube.

6. A ventilating device as claimed in claim 2, wherein said respiratory connector comprises a endotracheal tube.

7. A ventilating device as claimed in claim 2, wherein said respiratory connector comprises a esophageal obturator airway connection.

8. A ventilating device as claimed in claim 1, further comprising:

a positive end expiratory pressure valve connected to said air outlet; and means for adjusting said positive end expiratory pressure valve.

9. A ventilating device as claimed in claim 1, further comprising:

a third opening into said resilient airbag;

an attachable reservoir connection connected to said third opening;

an expandable reservoir air bag;

wherein said attachable reservoir connection allows for the connection of an attachable reservoir, such as an oxygen reservoir to increase the oxygen content of the air in said resilient airbag.

10. A ventilating device as claimed in claim 2, further comprising a third one-way valve located between said first airtube end of said airtube and said air outlet so as to allow a portion of the air going from said airtube to said air outlet to pass therethrough and exit said airtube and said air outlet while preventing any portion of the air going from said air outlet to said airtube to pass therethrough, wherein any portion of air passing through said one-way valve produces a noise.

11. A ventilating device as claimed in claim 2, wherein said means for collapsing said airbag includes one or more guy wires connected to the inside wall of said resilient airbag and wherein said actuator means during each cycle places tension on each of said guy wires during each first predetermined period of time to move each of said guy wires said predetermined distance radially toward said center axis and, during said second predetermined period of time, releases said tension causing said resilient airbag to return to its normally expanded shape, thereby pulling each of said guy wires said second direction the same predetermined distance.

12. A ventilating device as claimed in claim 11, further comprising:

a hollow tube located along said center axis having holes, wherein each of said guy wires pass through one of said holes to enter into said hollow tube; and are all connected; said second opening and a substantially airtight opening on said resilient airbag for allowing guy wires to enter therethrough from said second airbag and exit said airbag, wherein said actuator means further comprises means for receiving the guy wire portion which exits the interior of said airbag from said substantially airtight opening to move said plurality of guy wires.

13. A ventilating device as claimed in claim 12, wherein said actuator means further comprises:

a timing box having a first wall and a second wall connected to said airbag for receiving said guy wire portions;

a drive connection a drive means for imparting motion to said drive connection a drive connector attached to said timing box for receiving said motion from said drive connection, thereby imparting said motion to said drive connector, wherein said timing box contains translation means for converting said motion received by said drive connector to a rectilinear motion of the guy wire portion within said hollow tube.

14. A ventilating device as claimed in claim 13, wherein said drive is an integral drive unit with an outer casing comprising therein:

rechargeable batteries;

recharging connectors for connecting to an external power source, said recharging connectors being accessible from outside said outer casing;

recharging circuitry having an input connected to said recharging connectors and an output connected to said rechargeable batteries for recharging said batteries when said external power source is connected to said recharging connectors;

a rotary electric motor having a rotatable shaft, wherein said drive connection is attached to an end of said shaft;

control circuitry connected to said rechargeable batteries and said rotary electric motor; and one or more manually operated switches connected to said control circuitry, said one or more manually operated switches being accessible from outside said outer casing.

15. A ventilating device as claimed in claim 14, wherein said drive connector comprises a first rotary head having one or more first extended portions thereon, wherein said drive connection comprises a second rotary head comprising one or more first indentations thereon for mating with said one or more first extended portions, and wherein said ventilating device further comprises means for locking said drive connection to said drive connector once said one or more first extended portions are inserted into said one or more first indentations.

16. A ventilating device as claimed in claim 15, further comprising:

a flexible tubing having first and second end portions;

a flexible wire within said flexible tubing;

a first rotary head connected to one end of said flexible wire located at said first end portion of said flexible tubing, said first rotary head having one or more second extended portions thereon; and a second rotary head connected to the other end of said flexible wire located at said second end portion of said flexible tubing, said second rotary head having a second one or more indentations thereon, wherein a rotation of said first rotary head causes an equal amount of rotation in said second rotary head and visa versa;

wherein said ventilating device further comprises means for locking said first end portions of said flexible tubing to said drive connection once said one or more second extended portions are inserted into said one or more first indentations; and means for locking said second end portion second end of said flexible tubing to said drive connector once said one or more first extended portions are inserted into said one or more second indentations.

17. A ventilating device as claimed in claim 16, further comprising:

a belt attachable to the patient connected to said first respiratory end; and means for attaching said integral drive unit to said belt.

18. A ventilating device as claimed in claim 13, wherein said translation means further comprises:

a first bearing attached to said first wall of said timing box;

a drive connector shaft attached to said drive connector and passing through said first bearing;

a first shaft having a first end and a second end;

means for attaching said drive connector shaft to one end of one shaft;

a second bearing attached to said second wall of said timing box opposite said first wall, where said second bearing is attached to said second end of said first shaft;

a main gear slide ably attached to said first shaft, wherein a rotation of said first shaft causes an equal amount of angular rotation of said main gear;

a toothed region of said main gear starting at a first tooth of said gear and ending with a last tooth of said main gear;

a smooth region of said main gear starting just after said last tooth of said main gear and ending just before said first tooth of said main gear;

a third bearing attached to said first wall of said timing box adjacent to said first bearing;

a fourth bearing attached to said second wall adjacent to said second bearing;

a second shaft having a first end attached to said third bearing and a second end attached to said fourth bearing;

a plurality of air volume control gears rigidly attached to said second shaft for controlling the volume of air supplied to a patient connected to said first respiratory end during each cycle;

a manually operated slide attached to said main gear and adjustable to a plurality of discrete positions, each position placing the main gear in contact with one of said plurality of air volume control gears;

a fifth bearing attached to said first wall adjacent to said third bearing;

a sixth bearing attached to said second wall adjacent to said fourth bearing;

a third shaft having a first end attached to said fifth bearing and a second end attached to said sixth bearing;

a cam rigidly attached to said third shaft having a cam surface;

means for attaching said guy wire portion which exits said airbag from said substantially airtight opening to said cam;

a first transfer gear attached to said second shaft;

a second transfer gear attached to said third shaft and in contact with said first transfer gear;

a spring attached to said first wall and said third shaft for applying an angular force on said third shaft proportional to the displacement of said second shaft from a predetermined angular position, wherein each of said plurality of air volume control gears have a toothed region between respective first teeth and last teeth thereof, and a smooth region between just after the last tooth and just before the first tooth, wherein said predetermined angular position places each of said plurality of air volume control gears in a position such that said main gear is in contact with a first tooth of one of said volume control gears for each discrete position of said manually operated slide at the beginning of each first predetermined period of time of each cycle, wherein, during said first predetermined time period, said motion imparted to said drive connector by said drive connection causes a rotation of said drive connector and said drive connector shaft.

19. A ventilating device as claimed in claim 13, wherein said translation means further comprises:

a first bearing attached to said first wall of said timing box;

a second bearing attached to said second wall of said timing box opposite said first wall;

a drive connector shaft attached to said drive connector and passing through said first bearing;

a cam shaft with a cam rigidly connected thereto, wherein one end of said cam shaft is attached to said drive connector shaft and the other end of said cam shaft is connect to said second bearing;

means for attaching said guy wire portions which exit said airbag from said substantially airtight opening to said cam, wherein said drive comprises means for manually adjusting said predetermined distance to allow a user to control the volume of air supplied to a patient connected to said first respiratory end during each cycle, and wherein said drive further comprises means for adjusting said first predetermined period of time and said second predetermined period of time so as to allow a user to control the length of time between each cycle.

20. A ventilating device comprising:

a resilient airbag having means for biasing said airbag to a normally expanded state and said airbag being collapsible about a center axis, said resilient airbag further having a first airbag end and a second airbag end located along said center axis;

a first airbag opening at said first airbag end;

a first tube having a first end and a second end;

means for sealingly attaching the first end of said first tube to said airbag opening;

a circular partition located within said first tube adjacent said first end of said first tube;

a circular cutout located in the center of said circular partition;

a second tube having a first end and a second end;

means for attaching the first end of said second tube over said circular cutout and within said first tube;

a flexible extension tube having a first end and a second end;

a respiratory connector having a first respiratory end connectable to a patient and a second respiratory end having an air passageway in fluid communication with said first respiratory end;

means for attaching said second end of said respiratory connector to said first end of said flexible extension tube;

means for attaching said second end of said second tube to said second end of said flexible extension tube;

a reservoir volume bag having a first reservoir opening and a second reservoir opening;

means for attaching said first reservoir opening to said second end of said respiratory connector;

means for attaching said second reservoir opening to said second end of said first tube;

a plurality of airbag inlet openings located on said circular partition;

a plurality of first tube openings located on said first tube;

an oxygen inlet attached to said first tube and connectable to an external oxygen source;

an inlet one-way valve means attached over said plurality of first tube openings for allowing air to enter said resilient airbag through said plurality of airbag inlet openings while preventing air from exiting said resilient airbag through said plurality of airbag inlet openings;

an outlet one-way valve means attached to said respiratory connector adjacent said first respiratory end for allowing air to exit said resilient airbag through said first respiratory end while preventing air from entering said resilient airbag through said first respiratory end;

a plurality of mechanical attachments connected to said resilient airbag, said attachments including means for collapsing said airbag when moved in a first direction; and actuator means for cyclically engaging said means for collapsing such that said plurality of mechanical attachments move a predetermined distance in said first direction for a first predetermined period of time to overcome said means for biasing said airbag and subsequently disengaging said means for collapsing, thereby allowing said means for biasing said airbag to expand said airbag for a second period of time, wherein air enters said resilient airbag through said air inlet and said mechanical attachments move said predetermined distance in a second direction opposite said first direction.

* * * * *